(12) United States Patent
Kolb et al.

(10) Patent No.: US 8,798,705 B2
(45) Date of Patent: Aug. 5, 2014

(54) MEDICAL INSTRUMENT FOR DELIVERY OF HIGH VOLTAGE PULSES AND METHOD OF DELIVERING THE SAME

(75) Inventors: Juergen F. Kolb, Norfolk, VA (US);
Karl H. Schoenbach, Norfolk, VA (US);
Stephen P. Beebe, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 475 days.

(21) Appl. No.: 13/264,729

(22) PCT Filed: Apr. 14, 2010

(86) PCT No.: PCT/US2010/031014
§ 371 (c)(1),
(2), (4) Date: Jan. 19, 2012

(87) PCT Pub. No.: WO2010/120866
PCT Pub. Date: Oct. 21, 2010

(65) Prior Publication Data
US 2012/0109263 A1    May 3, 2012

Related U.S. Application Data

(60) Provisional application No. 61/253,306, filed on Oct. 20, 2009, provisional application No. 61/169,013, filed on Apr. 14, 2009.

(51) Int. Cl.
*A61B 5/04*       (2006.01)
(52) U.S. Cl.
USPC ............................................. 600/372; 607/2

(58) Field of Classification Search
CPC .................................................. B01L 2300/024
USPC ................................................ 600/372; 607/2
See application file for complete search history.

(56) References Cited

U.S. PATENT DOCUMENTS

| 5,873,849 A | 2/1999 | Bernard |
| 6,678,556 B1 * | 1/2004 | Nolan et al. ..................... 604/21 |
| 2006/0058782 A1 | 3/2006 | Truckai et al. |
| 2006/0135955 A1 | 6/2006 | Shadduck |

FOREIGN PATENT DOCUMENTS

WO       0054683 A1    9/2000

\* cited by examiner

*Primary Examiner* — Nicole F Lavert
(74) *Attorney, Agent, or Firm* — Novak Druce Connolly Bove + Quigg LLP

(57) ABSTRACT

An instrument 10 for delivering a high voltage pulse to tissue is disclosed. The instrument 10 can include an outer support member 12 with a liquid reservoir 14 that has a liquid-contacting interior surface 16, an opening 18 at a distal end 20 of the outer support member 12, and a ground electrode 22 extending in a longitudinal direction and having a lower surface 23 proximate the opening 18. The instrument 10 can also include a working electrode 26 extending longitudinally from the liquid-contacting interior surface 16 with a needle-shaped distal portion 28 proximate the distal end 20; and an inlet port 31 and an outlet port 34 in liquid communication with the liquid reservoir 14. The working electrode 26 can be electrically isolated from the ground electrode 22 by an insulating portion 30 of the outer support member 12, and a direct path can exist through the liquid reservoir 14 between the ground electrode 22 and the working electrode 26.

20 Claims, 7 Drawing Sheets

FIG. 8B

MEDICAL INSTRUMENT FOR DELIVERY OF HIGH VOLTAGE PULSES AND METHOD OF DELIVERING THE SAME

CROSS REFERENCE TO RELATED APPLICATIONS

This application is a §371 national phase entry of International Application No. PCT/US2010/31014, filed Apr. 14, 2010, which claims priority to U.S. Provisional Patent Application No. 61/169,013, filed Apr. 14, 2009, and U.S. Provisional Application No. 61/253,306, filed Oct. 20, 2009, the entire contents of which are incorporated herein by reference.

FIELD OF THE INVENTION

The present invention is related to medical instruments and methods designed to deliver pulsed electric fields to target tissue while minimizing collateral damage to surrounding tissue.

BACKGROUND

The exposure of biological cells to an electric field can change the morphology and the function of the cell. The nature and extent of these changes depends foremost on the duration of the exposure and the strength of the applied electric field. The predominant primary response is the charging of cell envelope and subcellular membranes. When a potential difference across the membrane above a certain threshold is eventually reached, membrane lipids become perturbed and as the perturbation is sustained, pores will start to open, enabling molecular transport. Long pulses, i.e. with durations of microseconds or milliseconds, are frequently used as a tool to introduce large molecules such as drugs and DNA into the cell in this manner. With the accumulation of ions along the cell envelope, the potential difference across the membrane increases and the electric field inside the cell is reduced simultaneously.

SUMMARY

The present invention overcomes the drawbacks of prior art medical instruments and techniques by providing new medical instruments, systems and techniques for delivery of pulsed electric fields to target subsurface tissue that minimizes collateral damage to surrounding tissue. In one embodiment, a medical instrument is disclosed for delivering a high voltage pulse to tissue. The medical instrument can include an outer support member with a liquid reservoir that has a liquid-contacting interior surface, an opening at a distal end of the outer support member, and a ground electrode extending in a longitudinal direction and having a lower surface proximate the opening. The medical instrument can also include a working electrode extending longitudinally from the liquid-contacting interior surface with a needle-shaped distal portion proximate the distal end. The medical instrument can also include an inlet port and an outlet port in liquid communication with the liquid reservoir, in which the working electrode is electrically isolated from the ground electrode by an insulating portion of the outer support member, and a direct path exists through the liquid reservoir between the ground electrode and the working electrode. The working electrode, the ground electrode, or both can also be replaceable.

The ground electrode can extend longitudinally from a perimeter-portion of the outer support member or the ground electrode can extend from the liquid-contacting interior surface. The ground electrode can also include at least one needle-shaped, tissue contacting portion extending longitudinally beyond the opening at the distal end of the outer support member.

The lower surface of the ground electrode can be a tissue-contacting surface. The tissue contacting surface can be symmetric along at least one axis extending through and perpendicular to a longitudinal axis of the hollow support member. For example, the tissue contacting surface can be a ring. The ground electrode can also include a plurality of electrically isolated ground electrode segments.

The needle-shaped distal portion of the working electrode can extend longitudinally beyond the opening at the distal end of the outer support member. The working electrode can also include an exposed portion that is not coated with an electrical insulator. The liquid-contacting interior surface of the liquid reservoir can include a lateral surface and a base surface, with the working electrode extending from the base surface, and the base surface can be convex.

A system for delivering a high voltage pulse to subsurface tissue is also disclosed herein. The system can include a medical instrument comprising an outer support member with a liquid reservoir comprising a liquid-contacting interior surface, an opening at a distal end of the outer support member, and a ground electrode extending in a longitudinal direction and having a lower surface proximate the opening; a working electrode extending longitudinally from the liquid-contacting interior surface and having a needle-shaped distal portion proximate the distal end; and an inlet port and an outlet port in liquid communication with the liquid reservoir. The working electrode can be electrically isolated from the ground electrode by an insulating portion of the outer support member, and a direct path can exist through the liquid reservoir between the ground electrode and said working electrode. The system can also include a power supply coupled to the ground electrode and the working electrode for applying electrical signals to provide high voltage pulses to subsurface tissue. The power supply can be a pulse generator. The system can deliver a corona discharge or plasma discharge to the subsurface tissue with no arcing between the working electrode and the ground electrode.

In another embodiment, the invention is drawn to a method for delivering a high voltage pulse to subsurface tissue. The method can include providing a medical instrument as described above, and inserting a portion of the working electrode into subsurface tissue of a mammalian subject. The method can also include supplying a liquid to the liquid reservoir to completely fill the liquid reservoir; and applying a pulse creating a voltage difference between the ground electrode and the working electrode of 1 kV to 100 kV. The pulse can be about 100 picoseconds to about 1 microsecond in duration and the voltage difference can between 5 kV and 40 kV. The method can also include producing a corona discharge or plasma discharge in subsurface tissue with no arcing between the working electrode and the ground electrode. The method can also include the lower surface of the ground electrode in contact with a tissue surface of the mammalian subject.

BRIEF DESCRIPTION OF THE DRAWINGS

The invention is described with more particularity below. The scope of this invention may be better understood by referring to the following description taken in conjunction with the accompanying drawings, in which.

DETAILED DESCRIPTION

Medical instruments, systems and methods disclosed herein are designed to deliver high-voltage pulses to target subsurface tissue without causing thermal or electrical damage to the surface of the tissue. In particular, the instruments, systems and methods disclosed herein include a medical instrument having a liquid reservoir surrounding exposed portions of the working electrode(s) and ground electrode(s) used to deliver the high-voltage pulses, which can result in delivery of corona or plasma discharges, without surface tissue damage. The high-voltage is applied to the electrodes using a nanosecond pulse, which enables the use of nearly any fluid to serve as an insulator preventing arcing over the surface of the tissue being treated. As used herein, the phrase "high-voltage pulses" relates generally to voltage differences ranging from about 1 kV to about 100 kV or even higher applied for a duration from about 100 picoseconds to about 1 microsecond.

In one embodiment shown in FIGS. 1-4, the medical instrument 10 for delivering a high-voltage pulse to tissue (A) can include an outer support member 12 comprising a liquid reservoir 14 that has a liquid-contacting interior surface 16, and an opening 18 at a distal end 20 of the outer support member 12, and a ground electrode 22 extending in a longitudinal direction and having a lower surface 23 proximate the opening 18. The lower surface 23 can be a tissue-contacting surface 24. The medical instrument can have a longitudinal axis 21 and the ground electrode 22 can extend longitudinally. The medical instrument 10 can also include a working electrode 26 extending longitudinally from the liquid-contacting interior surface 16 and having a needle-shaped distal portion 28 proximate the distal end 20. The working electrode 26 is electrically isolated from the ground electrode 22 by an insulating portion 30 of the outer support member 12. A direct path exists through the liquid reservoir 14 between the ground electrode 22 and the working electrode 26.

Exemplary electrical insulators that can be used for the insulating portion 30 include, but are not limited to, poly(p-xylylene), polyimide, and fluoropolymers. Exemplary fluoropolymers include polytetrafluoroethylene, such as that sold under the TEFLON mark, and other polymers, ceramics and coatings useful as electrical insulators, and exemplary poly (p-xylylene) polymers include those sold by Para Tech Coating, Inc., under the PARYLENE trademark.

The medical instrument 10 can also include an inlet port 31 and an outlet port 34 in liquid communication with the liquid reservoir 14. Tubing 36 can be connected to the inlet port 31 and the outlet port 34. A pump 38 can be connected to the tubing 36 connected to the inlet port 31, the outlet port 34, or both. In general, the pump 38 will not re-circulate liquid to the liquid reservoir 14.

Figure 1:
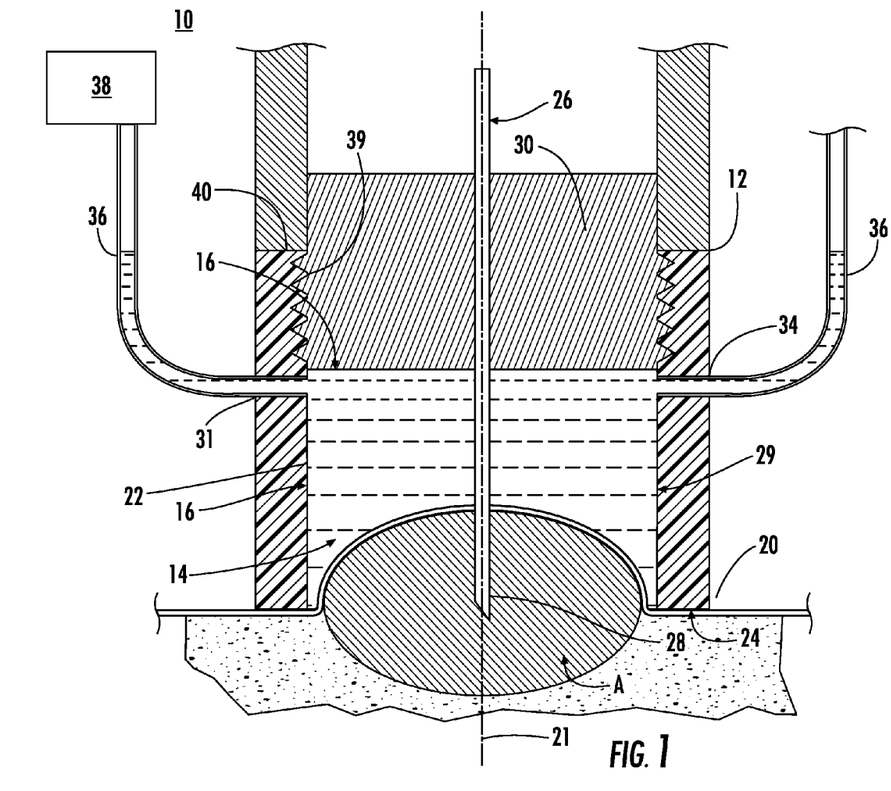
FIG. 1 is a cross-sectional view of an exemplary medical instrument for delivering high voltage treatment to subsurface tissue.
Figure 8A:
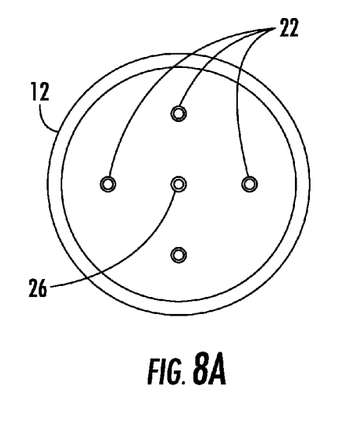
FIG. 8A is a bottom view of a first exemplary geometry of the ground electrode and the working electrode, where the ground electrode includes a plurality of needle shaped ground electrodes.
Figure 8B:
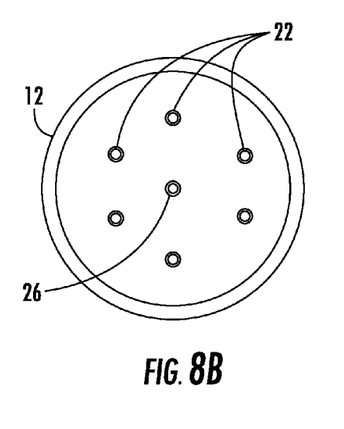
FIG. 8B is a bottom view of a second exemplary geometry of the ground electrode and the working electrode, where the ground electrode includes a plurality of needle shaped ground electrodes.

As shown in FIG. 1 and also in FIGS. 8A and 8B, the ground electrode 22 can extend longitudinally at a perimeter-portion of the outer support member 12. The needle-shaped distal portion 28 of the working electrode 26 can extend longitudinally beyond the opening 18 of the liquid reservoir 14. As used herein, the "perimeter-portion" includes those portions adjacent the radial exterior 39, 40 of the outer support member 12, for example an outer hollow, cylindrical housing as shown in FIGS. 1-4. It is to be understood that the perimeter-portion can include longitudinally-extending surfaces, laterally-extending surfaces, or both of the outer support member 12. For example, in FIG. 1, the ground electrode 22 extends from both a longitudinally-extending portion 39 of the outer support member 12, i.e., the threaded portion of the insulating portion 30, and a laterally-extending portion 40 of the outer support member 12.

Figure 4:
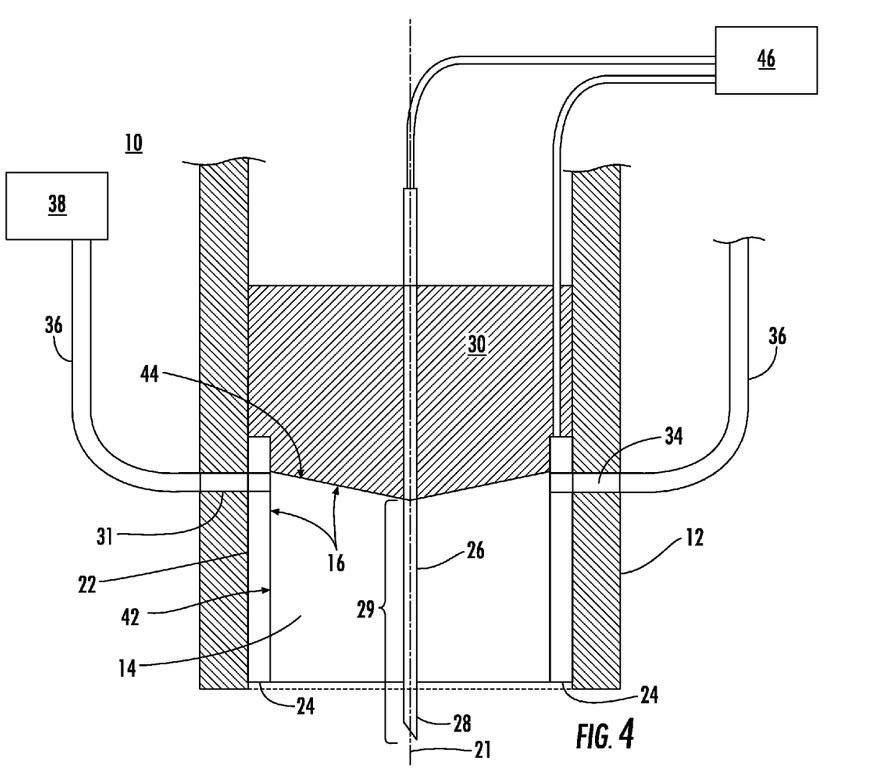
FIG. 4 is a cross-section view of an exemplary medical instrument for delivering high voltage treatment to subsurface tissue where the ground electrode is a hollow cylinder forming the lateral sides of the liquid reservoir.

The liquid-contacting interior surface 16 can include a lateral surface 42 and a base surface 44, with the working electrode 26, the ground electrode 22, or both, extending from the base surface 44. As shown in FIG. 4, the ground electrode 22 can extend from the base surface 44 and at a perimeter portion of the outer support member 12.

Figure 2:
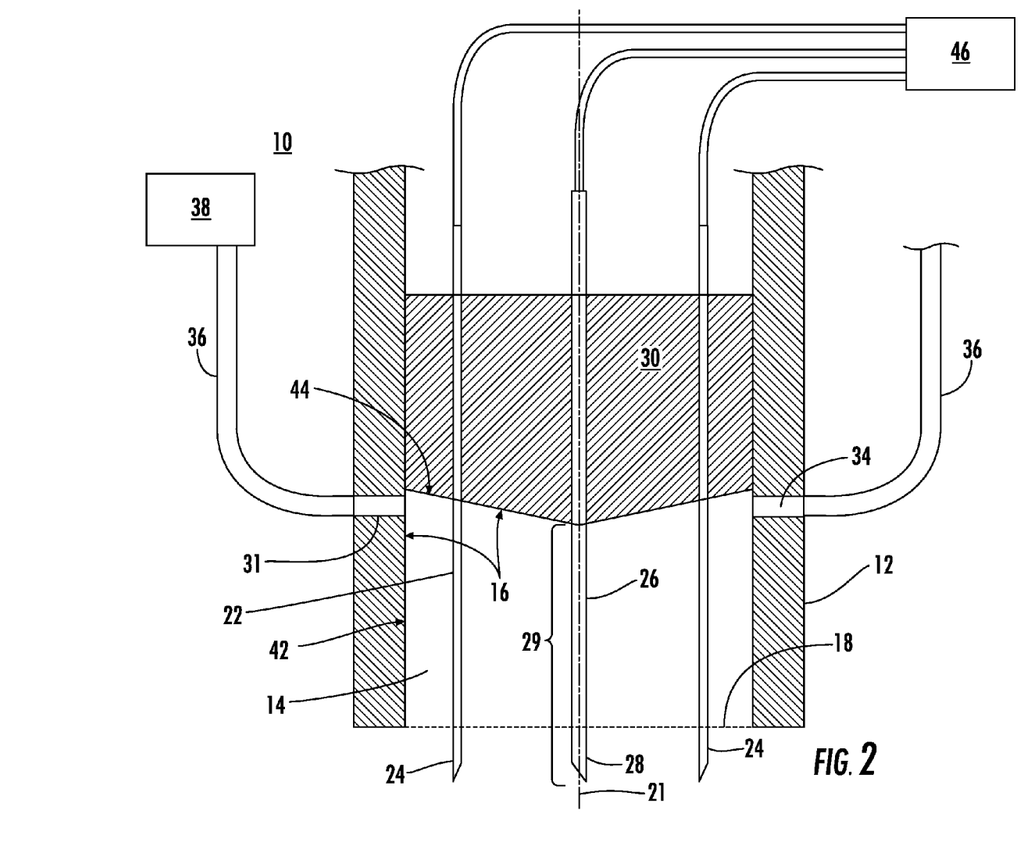
FIG. 2 is a cross-section view of an exemplary medical instrument for delivering high voltage treatment to subsurface tissue where the ground electrode is a plurality of needles surrounding the working electrode.
Figure 3:
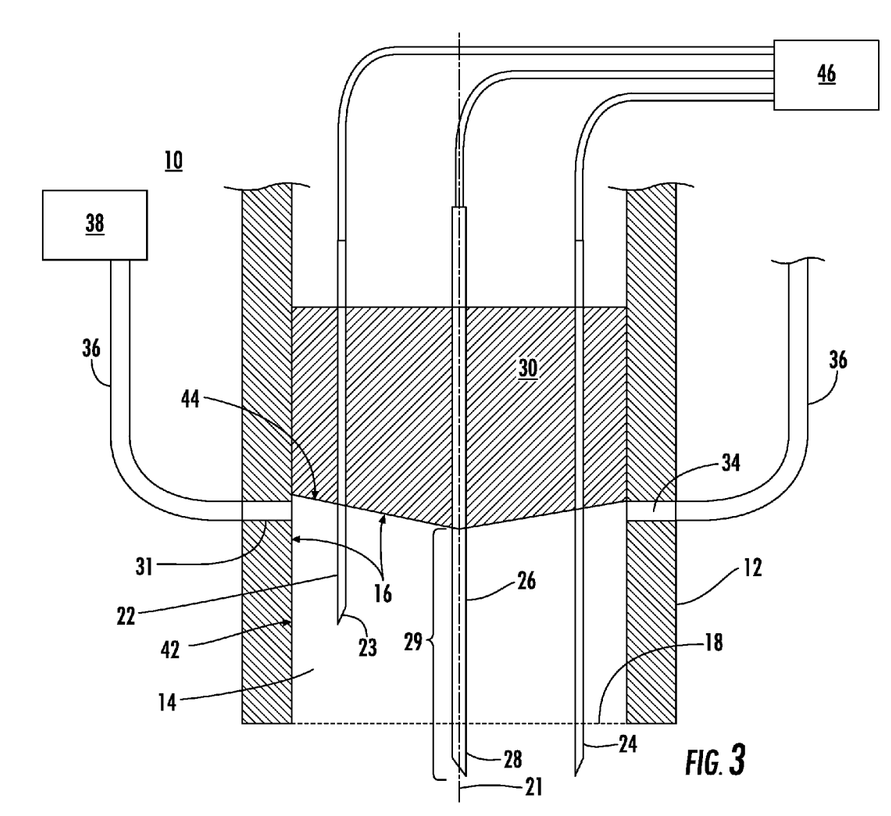
FIG. 3 is a cross-section view of an exemplary medical instrument for delivering high voltage treatment to subsurface tissue where the ground electrode is a plurality of needles surrounding the working electrode.

As shown in FIGS. 2-4, the base surface 44 can be convex. These configurations with the inlet and outlet ports 31, 34 adjacent the highest points of the liquid reservoir 14 can be designed to help ensure that no air or other gas is in contact with the working electrode 26 and that there is no direct path through air or another gas between the working electrode 26 and another conductor, e.g., the ground electrode 22. Such a configuration can be beneficial in order to prevent arcing between the working electrode 26 and the ground electrode 22 or another conductor.

As shown in FIG. 2, the ground electrode 22 can extend longitudinally from the liquid-contacting interior surface 16 of the liquid reservoir 14. The ground electrode 22 can include at least one needle-shaped, tissue contacting portion 24 extending longitudinally beyond the opening 18. FIG. 8 shows bottom views of such configurations using a needle-shaped working electrode 26 surrounded by a plurality of needle-shaped, ground electrodes 22.

As shown in FIG. 3, the ground electrode 22 does not necessarily have a tissue-contacting surface. In such instances, the ground electrode 22 can extend longitudinally and have a lower surface proximate the opening 18. The ground electrode(s) 22 can have any useful shape including, but not limited to (i) a flat ring, e.g., a washer, (ii) a hollow cylinder, as shown in FIGS. 1 and 4, and (iii) a plurality of needle-shaped protrusions, as shown in FIGS. 2, 3 and 8.

The high-voltage pulses applied using the instrument and system disclosed herein can produce nanosecond pulsed electric fields, corona discharges or plasma discharges depending on a variety of factors that include, but are not limited to, the configuration of the electrodes 22, 26, the duration of the pulse, and the voltage applied to the electrodes 22, 26. In addition, it has been discovered that corona or plasma discharges are easier to produce using a ring or hollow, cylindrical ground electrode, whereas it is easier to avoid corona or plasma discharges, i.e., produce pulsed electric fields, using needle-shaped ground electrodes.

The working electrode 26, the ground electrode 22, or both 22, 26 can be replaceable. An exposed portion 29 of the working electrode 26 can be free of any electrically insulating coating. As used herein the "exposed portion" of an electrode is meant to refer to the portion of the electrode 22, 26 extending longitudinally beyond the liquid-contacting interior surface 16.

The electrodes 22, 26 can comprise an electrical conductor that is resistant to corrosion, e.g., stainless steel. The tissue contacting surface 24 of the ground electrode 22 and the working electrode 26 can be electropolished or otherwise planarized or smoothed. Electropolishing removes corners and sharp edges. Polishing in general is used to provide a smoother surface for charges to reside upon and to eliminate sharp edges that focus and enhance the electric field in that region.

The working electrode 26, the ground electrode 22, or both 22, 26, can have a cylindrical, needle shape. In such instances, the electrodes 22, 26 can have a diameter 38 of about 1 mm or less, about 0.75 mm or less, about 0.5 mm or less, or about 0.3 mm or less. All other variables being constant, the electric field in the subsurface tissue proximate the working electrode 26 will increase as the diameter of the working electrode 26 decreases.

The working electrode 26, the ground electrode 22, or both, can be solid or hollow, such as a needle. Where the working electrode 26 or ground electrode 22 are hollow, the hollow cavity within the electrode 22, 26 can be connected to an injection reservoir, as in a hypodermic needle, used to inject active and inert ingredients to supplement the high voltage discharge treatments.

Figures 5A, 5B, 5C, 5D, 5E:
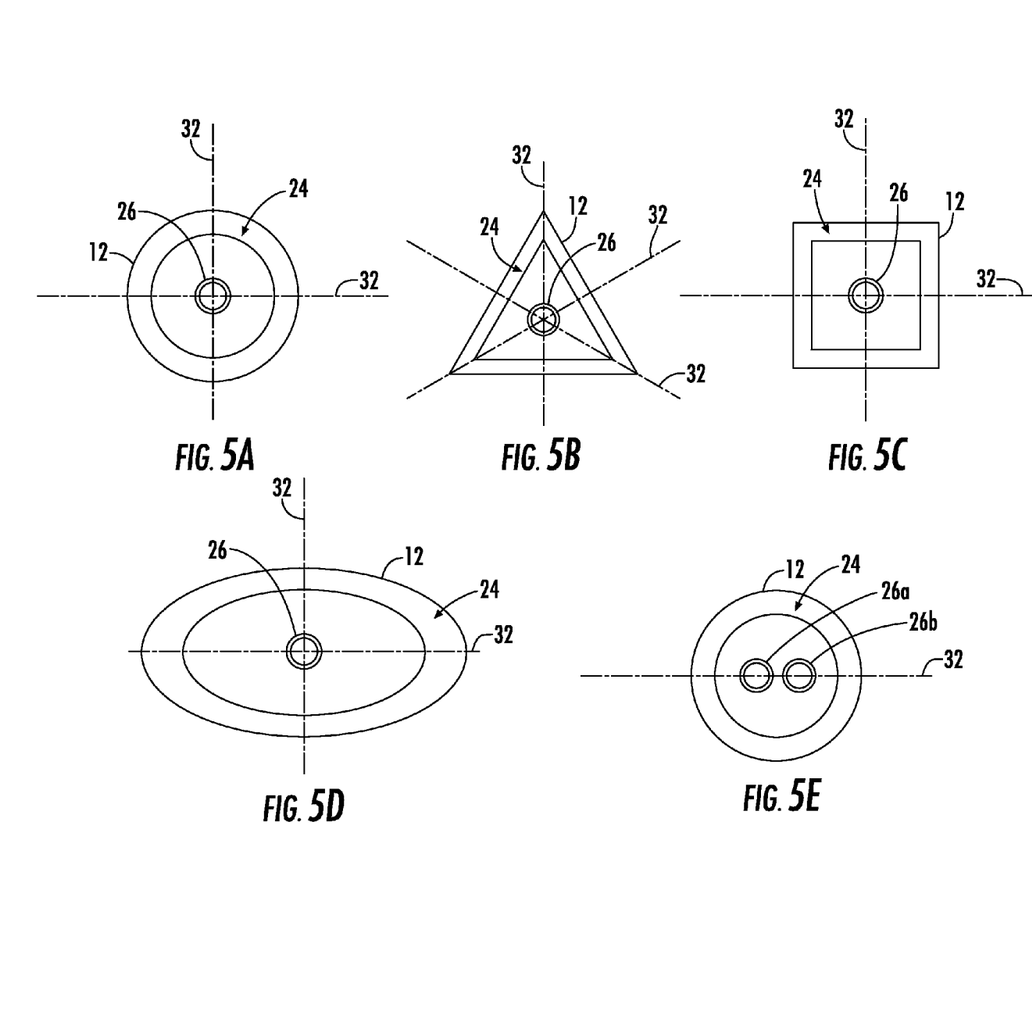
FIGS. 5(a)-(e) are bottom views of several exemplary geometries of ground electrode(s) and the working electrode(s) that can be used in the exemplary medical instruments disclosed herein.

As shown in FIGS. 5(*a*)-(*d*), the ground electrode 22 can have a tissue contacting surface 24 that is symmetrical along at least one axis 32 passing through the longitudinal axis 21 of the outer support member 12. The ground electrode 22 can have a tissue contacting surface 24 that is symmetrical along at least two axes 32 passing through the longitudinal axis 21. As shown in FIGS. 5(*a*), (*c*) and (*d*), the ground electrode 22 can have a tissue contacting surface 24 that is symmetrical along two orthogonal axes 32 passing through the longitudinal axis 21. It will be appreciated that FIGS. 5(*a*)-(*e*) do not show all possible axes of symmetry 32. For example, FIG. 5(*c*) has at least 4 axes of symmetry passing through the longitudinal axis 21. Such embodiments are typically those where the ground electrode 22 extends longitudinally from a perimeter-portion of the outer support member 12.

As shown in FIG. 5(*e*), the medical instrument 10 can include more than one working electrode 26 disposed within the perimeter of the ground electrode 22. Where the medical instrument 10 includes more than one working electrode 26, each of the working electrodes 26 can be wired so that working electrodes 26(*a*), 26(*b*) can remain at the same voltage. If there is more than one working electrode 26, the working electrodes 26(*a*), 26(*b*) can be wired so that they can be energized simultaneously or separately at the same or different voltages. As shown in FIG. 5(*e*), when the medical instrument 10 includes multiple working electrodes 26, the ground electrode 22 can have a tissue contacting surface 24 that is symmetrical along at least one axis 32 passing through a longitudinal axis of the more than one working electrodes 26(*a*), 26(*b*).

The ground electrode 22 can have any number of possible shapes, including circle, ellipse, oval, triangle, and polygons, such as squares, pentagons, hexagons, heptagons, etc. The shape of the ground electrode 22 can be such that the nanopulses create a generally symmetric electrical field around the working electrode 26.

Figure 6A:
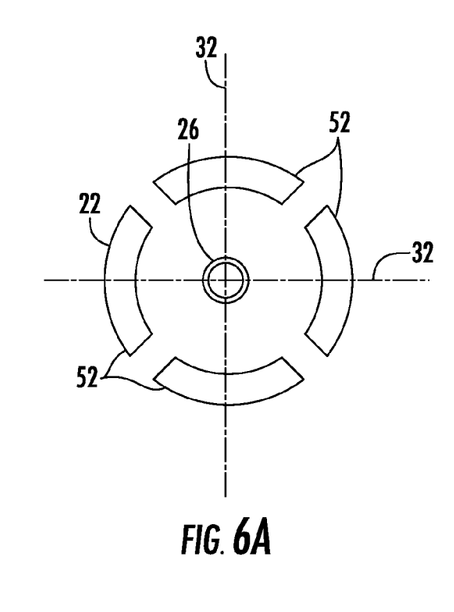
FIGS. 6(a)-(c) are bottom views of several exemplary geometries of the ground electrode and the working electrode where the ground electrode includes a plurality of ground electrode segments.
Figure 6B:
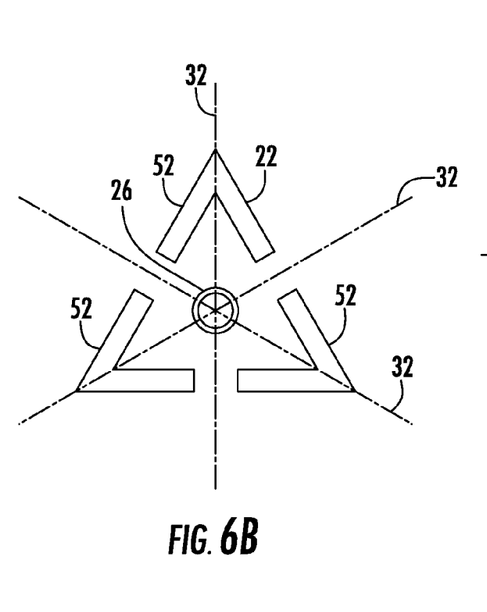
Figure 6C:
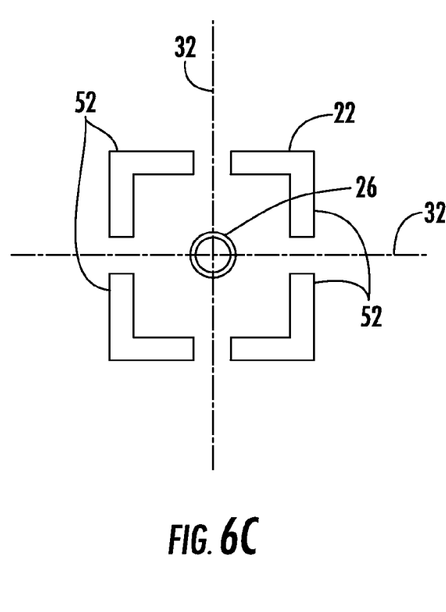

As shown in FIGS. 6(*a*)-(*c*), the ground electrode 22 can include a number of segments 52. At least one ground electrode segment 52 can be electrically isolated from another ground electrode segment 52 and at least two ground electrode segments 52 can be connected to separate electrically conductive wires operably connected to a power supply (not shown). This configuration enables the at least two ground electrode segments 52 and the working electrode(s) 22 to be energized simultaneously or separately at the same or different voltages.

Figure 7:
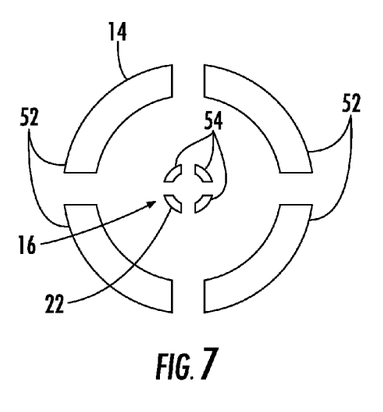
FIG. 7 is a bottom view of an exemplary geometry of the ground electrode and working electrode, where the ground electrode includes a plurality of ground electrode segments and the working electrode includes a plurality of working electrode segments.

Similarly, as shown in FIG. 7, the working electrode can include a number of electrically insulated segments 54 that are operably connected to a power supply using separate electrical connections (not shown). This configuration enables the at least two ground electrode segments 52 and the at least two working electrode segments 54 to be energized simultaneously or separately at the same or different voltages.

A system for delivering a corona discharge to subsurface tissue is also disclosed. The system includes the medical instrument 10 having a liquid reservoir 14, a ground electrode 22, a working electrode 26, an inlet port 31 and an outlet port 34. In addition, the system can include a power supply 46 electrically coupled to the ground electrode 26 and the working electrode 22 for applying a voltage difference therebetween. The system can include a pump for supplying a fluid to the liquid reservoir 14. The power supply 46 can be a pulse generator.

A variety of power supplies 46 can be used with the present invention. An exemplary power supply 46 is a pulsed power supply capable of delivering nanosecond high voltage pulses which are imposed across the ground electrode 22 and the working electrode 26, to generate electrical fields on the order of 1 to 100 kV/cm. One suitable power supply 46 arrangement for generating the necessary pulses to medical devices 10 according to the invention are disclosed in U.S. patent application Ser. No. 12/418,864 entitled "DELIVERY DEVICE, SYSTEM, AND METHOD FOR DELIVERING NANOSECOND PULSED ELECTRIC FIELDS" filed on Apr. 6, 2009, the entirety of which is hereby incorporated herein by reference.

The power supply 46 can include a pulse generator capable of producing pulse durations of about 1 microseconds or less, or ranging in duration from about 0.5 microsecond to about 200 picoseconds, or from about 0.25 microsecond to about 1 nanosecond, or from about 10 nanoseconds to about 400 nanoseconds, or a range of any combination of pulse durations disclosed herein, e.g., about 1 microsecond to 150 nanoseconds. The nanosecond pulses applied in the associated method can have any of the above-identified ranges.

A method for delivering high voltage pulses to subsurface tissue using the medical instrument is also disclosed. The method includes inserting a portion of the working electrode 26 into subsurface tissue of a mammalian subject with the ground electrode 22 contacting a tissue surface. A liquid is then supplied to the liquid reservoir 14 to completely fill the liquid reservoir 14. Finally, a pulse is applied to create a voltage difference between the ground electrode 22 and the working electrode 26 of 1 kV to 100 kV. The method can include delivering a corona or plasma discharge to subsurface tissue. The method can also include delivering a pulsed electric field to the subsurface tissue.

The method disclosed herein can deliver a high voltage pulse, even a corona discharge, to subsurface tissue with no arcing between the working electrode and the ground electrode. It is believed that by using nanosecond pulses, particularly those less than 500 nanoseconds, it is possible to prevent arcing above the surface of the skin using the device and method disclosed herein. Although not wishing to be bound by theory, because such short pulses are used, the liquid prevents the formation of a plasma channel, even where it is a conductor, such as water or even saline solution.

As used herein, the term "contacting a tissue surface" is intended to encompass both touching a tissue surface as well as piercing, or penetrating, the tissue surface. In particular, in FIG. 1, the ground electrode 22 contacts, or touches, a tissue surface, whereas in FIG. 2, the ground electrode 22 penetrates or pierces a tissue surface. The term "contacting" is intended in describe both instances.

The pulse duration can be between about 100 picoseconds to about 1 microsecond. The nanosecond pulse can be at least 250 picoseconds, at least 500 picoseconds, at least 1 nanosecond, or at least 2 nanoseconds in duration. The nanosecond pulse can be less than 10 nanoseconds, less than 7 nanoseconds, less than 5 nanoseconds, or less than 3 nanoseconds in duration.

The voltage difference between the ground electrode 22 and the working electrode 26 can be about 1 to about 100 kV, or about 1 to about 70 kV, or about 1.5 to about 40 kV, or about 3 to about 30 kV or about 5 to about 30 kV, or about 10 to about 30 kV or about 15 to about 25 kV, or any combination thereof, e.g., about 1.5 to about 30 kV. The medical instrument 10 for delivering electrotherapy can be used to treat various conditions and target tissues including, but not limited to, tumors, such as carcinomas, lipomas, melanomas; cellulite; sweat glands; hair follicles; stem cells; fatty deposits; connective tissue and other conditions of the skin and subcutaneous tissues.

The foregoing is provided for purposes of illustrating, explaining, and describing embodiments of this invention. Modifications and adaptations to these embodiments will be apparent to those skilled in the art and may be made without departing from the scope or spirit of this invention.

The invention claimed is:

1. An instrument 10 for delivering a high voltage pulse, comprising:
    an outer support member 12 comprising a liquid reservoir 14 comprising:
        a liquid-contacting interior surface 16,
        an opening 18 at a distal end 20 of said outer support member 12, and
        a ground electrode 22 extending in a longitudinal direction and having a lower surface 23 proximate said opening 18;
    a working electrode 26 extending longitudinally from said liquid-contacting interior surface 16 and having a needle-shaped distal portion 28 proximate said distal end 20; and
    an inlet port 31 and an outlet port 34 in liquid communication with said liquid reservoir 14, wherein said working electrode 26 is electrically isolated from said ground electrode 22 by an insulating portion 30 of said outer support member 12, wherein a direct path exists through said liquid reservoir 14 between said ground electrode 22 and said working electrode 26.

2. The instrument 10 according to claim 1, wherein the lower surface 23 is a tissue-contacting surface 24.

3. The instrument 10 according to claim 1, wherein said ground electrode 22 extends longitudinally from a perimeter-portion of said outer support member 12.

4. The instrument 10 according to claim 2, wherein said needle-shaped distal portion 28 extends longitudinally beyond said opening 18.

5. The instrument 10 according to claim 1, wherein said ground electrode 22 extends from said liquid-contacting interior surface 16.

6. The instrument 10 according to claim 4, wherein said ground electrode 22 comprises at least one needle-shaped, tissue contacting portion extending longitudinally beyond said opening 18.

7. The instrument 10 according to claim 5, wherein said needle-shaped distal portion 28 extends longitudinally beyond said opening 18.

8. The instrument 10 according to claim 1, wherein said working electrode 26, said ground electrode 22, or both 26, 22 are replaceable.

9. The instrument 10 according to claim 1, wherein an exposed portion 29 of said working electrode 26 is not coated with an electrical insulator.

10. The instrument 10 according to claim 1, wherein a tissue contacting surface 24 of said ground electrode 22 is symmetric along at least one axis 32 extending through and perpendicular to a longitudinal axis 21 of the hollow support member.

11. The instrument 10 according to claim 1, wherein a tissue contacting surface 24 of said ground electrode 22 comprises a ring.

12. The instrument 10 according to claim 1, wherein said ground electrode 22 comprises a plurality of electrically isolated ground electrode segments 52.

13. The instrument 10 according to claim 1, wherein said liquid-contacting interior surface 16 comprises a lateral surface 42 and a base surface 44, said working electrode 26 extending from said base surface 44, wherein said base surface 44 is convex.

14. A system for delivering high voltage pulses, comprising:
    an instrument 10, comprising:
        an outer support member 12 comprising a liquid reservoir 14 comprising:
            a liquid-contacting interior surface 16,
            an opening 18 at a distal end 20 of said outer support member 12, and
            a ground electrode 22 extending in a longitudinal direction and having a lower surface 23 proximate said opening 18;
        a working electrode 26 extending longitudinally from said liquid-contacting interior surface 16 and having a needle-shaped distal portion 28 proximate said distal end 20; and
        an inlet port 31 and an outlet port 34 in liquid communication with said liquid reservoir 14, wherein said working electrode 26 is electrically isolated from said ground electrode 22 by an insulating portion 30 of said outer support member 12, wherein a direct path exists through said liquid reservoir 14 between said ground electrode 22 and said working electrode 26; and a power supply 46 coupled to said ground electrode 22 and said working electrode 26 for applying electrical signals to provide high voltage pulses to subsurface tissue.

15. The system according to claim 14, wherein said power supply 46 comprises a pulse generator.

16. The system according to claim 14, wherein a corona discharge or plasma discharge is delivered to said subsurface tissue with no arcing between said working electrode 26 and said ground electrode 22.

17. A method of delivering a high voltage discharge to tissue comprising,
   providing an instrument 10 according to claim 1;
   inserting a portion of the working electrode 26 into subsurface tissue,
   supplying a liquid to said liquid reservoir 14 to completely fill the liquid reservoir 14; and
   applying a pulse creating a voltage difference between the ground electrode 22 and the working electrode 26 of 1 kV to 100 kV.

18. The method according to claim 17, wherein the pulse is about 100 picoseconds to about 1 microsecond in duration.

19. The method according to claim 17, wherein the voltage difference is between 5 kV and 40 kV.

20. The method according to claim 17, wherein a corona discharge or plasma discharge is delivered to said subsurface tissue with no arcing between the working electrode 26 and the ground electrode 22.

* * * * *